US011262298B2

(12) United States Patent
Hodel et al.

(10) Patent No.: US 11,262,298 B2
(45) Date of Patent: Mar. 1, 2022

(54) SYSTEM AND METHOD FOR DETERMINING FLUID ORIGIN

(71) Applicant: Caterpillar Inc., Deerfield, IL (US)

(72) Inventors: Benjamin John Hodel, Dunlap, IL (US); Cynthia Marie Mann Rohde, Washington, IL (US)

(73) Assignee: Caterpillar Inc., Peoria, IL (US)

( * ) Notice: Subject to any disclaimer, the term of this patent is extended or adjusted under 35 U.S.C. 154(b) by 195 days.

(21) Appl. No.: 16/117,536

(22) Filed: Aug. 30, 2018

(65) Prior Publication Data

US 2020/0072743 A1 Mar. 5, 2020

(51) Int. Cl.
*G01N 21/3577* (2014.01)
*G01N 33/28* (2006.01)

(52) U.S. Cl.
CPC ..... *G01N 21/3577* (2013.01); *G01N 33/2888* (2013.01)

(58) Field of Classification Search
CPC .................... G01N 21/3577; G01N 33/28888
See application file for complete search history.

(56) References Cited

U.S. PATENT DOCUMENTS

| | | | | |
|---|---|---|---|---|
| 3,806,727 A | * | 4/1974 | Leonard ................. | G01N 21/64 250/301 |
| 4,657,144 A | * | 4/1987 | Martin ..................... | A24B 1/04 131/108 |

(Continued)

FOREIGN PATENT DOCUMENTS

| | | |
|---|---|---|
| CN | 101726451 A | 6/2010 |
| CN | 102830087 A | 12/2012 |

(Continued)

OTHER PUBLICATIONS

Meng,F. et al. "Characterization of Motor Oil by Laser-Induced Fluorescence"; Analytical Letters, vol. 48, Issue 13, Publication (online). 2015 (retrieved Oct. 17, 2019), Retrieved from the Internet: <URL: https://www.tandfonline.com/doi/full/10.1080/00032719.2015.1015703>; pp. 2090-2095; see entire document.

(Continued)

*Primary Examiner* — David P Porta
*Assistant Examiner* — Djura Malevic
(74) *Attorney, Agent, or Firm* — Harrity & Harrity LLP (57) ABSTRACT

A system for determining an origin of a fluid from a machine may include a spectral measurement device configured to generate spectral data for a fluid, and a transmitter in communication with the spectral measurement device and configured to transmit the spectral data. The system may also include a receiver in communication with the transmitter and configured to receive a transmission indicative of the spectral data from the transmitter. The system may further include a processor in communication with the receiver and configured to cause execution of an analytical model configured to determine, based at least in part on the spectral data, fluidic information related to the fluid, the fluidic information including an indication of an origin of the fluid. The system may also include an output device in communication with the processor and configured to output the indication of the origin of the fluid.

20 Claims, 4 Drawing Sheets

(56) References Cited

U.S. PATENT DOCUMENTS

| | | | |
|---|---|---|---|
| 5,537,336 A | 7/1996 | Joyce | |
| 5,554,480 A * | 9/1996 | Patel | G03G 9/0804 430/108.1 |
| 5,786,219 A * | 7/1998 | Zhang | G01N 15/1012 422/82.07 |
| 5,804,447 A * | 9/1998 | Albert | C09B 47/045 436/172 |
| 5,807,605 A * | 9/1998 | Tingey | G01N 21/643 118/713 |
| 5,974,860 A * | 11/1999 | Kuroda | G01M 3/38 73/40 |
| 5,998,211 A * | 12/1999 | Albert | C10L 1/003 436/56 |
| 6,025,200 A * | 2/2000 | Kaish | G01N 21/643 422/83 |
| 6,232,124 B1 * | 5/2001 | Selinfreund | G01N 21/6428 436/172 |
| 6,529,273 B1 * | 3/2003 | Norris | G01N 21/64 356/417 |
| 6,809,819 B1 * | 10/2004 | Vinjamoori | G01N 21/53 356/337 |
| 7,068,356 B2 * | 6/2006 | Saglimbeni | G01N 21/31 283/81 |
| 7,142,296 B2 * | 11/2006 | Cunningham | B01L 3/5085 356/326 |
| 7,172,903 B2 * | 2/2007 | Schilowitz | G01N 21/3151 250/343 |
| 7,241,621 B2 * | 7/2007 | Reischman | G01N 21/33 436/60 |
| 7,442,936 B2 * | 10/2008 | Reischman | G01N 21/552 250/339.12 |
| 7,671,983 B2 | 3/2010 | Shammai et al. | |
| 7,741,122 B2 * | 6/2010 | Reischman | G01N 33/287 436/60 |
| 7,749,438 B2 * | 7/2010 | Zeinali | G01N 21/77 422/402 |
| 7,919,325 B2 * | 4/2011 | Eastwood | G01N 21/6428 436/56 |
| 8,558,165 B2 | 10/2013 | Evans | G01V 5/10 250/269.2 |
| 9,080,987 B2 * | 7/2015 | Faenza | G01N 33/2882 |
| 9,174,245 B2 * | 11/2015 | Blanc | B07C 5/3422 |
| 9,361,561 B2 * | 6/2016 | Bown | G01N 21/94 |
| 9,791,407 B2 * | 10/2017 | Urey | C10L 1/003 |
| 9,804,142 B2 | 10/2017 | Basu et al. | |
| 9,995,681 B2 * | 6/2018 | Conroy | G01N 33/2882 |
| 10,330,607 B2 * | 6/2019 | Cadieux, Jr. | A24C 5/3412 |
| 10,365,239 B2 * | 7/2019 | Lilik | G01N 21/25 |
| 10,951,958 B1 * | 3/2021 | Arana | H04N 21/2541 |
| 11,019,076 B1 * | 5/2021 | Jakobsson | H04L 51/12 |
| 2001/0045378 A1 * | 11/2001 | Charles | B07C 5/3412 209/3.3 |
| 2002/0097833 A1 * | 7/2002 | Kaiser | G01N 23/223 378/45 |
| 2003/0141459 A1 * | 7/2003 | Hegazi | G01N 21/6408 250/461.1 |
| 2003/0194052 A1 * | 10/2003 | Price | G01N 23/223 378/45 |
| 2003/0194578 A1 * | 10/2003 | Tam | D01F 8/04 428/690 |
| 2004/0031931 A1 * | 2/2004 | Muller | G07D 7/12 250/458.1 |
| 2004/0085080 A1 * | 5/2004 | Schilowitz | G01N 27/026 324/698 |
| 2004/0227112 A1 * | 11/2004 | Howard | F41J 2/00 250/574 |
| 2004/0248307 A1 * | 12/2004 | Grof | G01N 33/2882 436/56 |
| 2005/0035755 A1 * | 2/2005 | Schilowitz | G01N 33/2888 324/698 |
| 2005/0110503 A1 * | 5/2005 | Koehler | G01N 27/026 324/710 |
| 2005/0178841 A1 * | 8/2005 | Jones, II | G07D 7/1205 235/468 |
| 2005/0184734 A1 * | 8/2005 | Sosnowski | G01N 27/026 324/444 |
| 2005/0241989 A1 * | 11/2005 | Sant | C10M 171/00 208/18 |
| 2006/0118741 A1 * | 6/2006 | Ross | C03C 3/095 250/556 |
| 2007/0023715 A1 * | 2/2007 | Ross | C03C 3/095 250/556 |
| 2007/0064323 A1 * | 3/2007 | Luther | G01N 21/64 359/890 |
| 2007/0178596 A1 * | 8/2007 | Babichenko | C10L 1/003 436/56 |
| 2007/0187617 A1 * | 8/2007 | Kong | G01N 21/6408 250/461.1 |
| 2009/0141961 A1 * | 6/2009 | Smith | G06K 9/00577 382/135 |
| 2010/0208243 A1 * | 8/2010 | Suzuki | G01N 33/2852 356/128 |
| 2010/0219377 A1 * | 9/2010 | Ebert | C09K 11/7771 252/301.4 S |
| 2010/0222917 A1 * | 9/2010 | Bohlig | B07C 5/342 700/224 |
| 2010/0226861 A1 * | 9/2010 | Cole | A61K 8/02 424/9.6 |
| 2011/0040503 A1 * | 2/2011 | Rogers | B67B 7/222 702/55 |
| 2011/0101094 A1 * | 5/2011 | Call | B67D 7/34 235/381 |
| 2011/0130882 A1 * | 6/2011 | Perez | G01N 33/2835 700/282 |
| 2011/0151576 A1 * | 6/2011 | Perfect | G01N 21/643 436/172 |
| 2011/0216190 A1 * | 9/2011 | Shimazu | B07C 5/342 348/135 |
| 2011/0229983 A1 * | 9/2011 | Wilkinson | G01N 21/3577 436/501 |
| 2012/0034702 A1 * | 2/2012 | Croud | G01N 33/2882 436/172 |
| 2012/0104278 A1 * | 5/2012 | Downing | G01N 21/6428 250/458.1 |
| 2012/0205449 A1 * | 8/2012 | Lewis | G06K 19/06037 235/468 |
| 2013/0009119 A1 * | 1/2013 | Natan | H01S 3/30 252/582 |
| 2013/0033701 A1 * | 2/2013 | Tunheim | G01N 21/85 356/73 |
| 2013/0124176 A1 * | 5/2013 | Fox | G06F 17/00 703/7 |
| 2013/0155402 A1 * | 6/2013 | Walton | G01J 3/0218 356/301 |
| 2013/0179090 A1 * | 7/2013 | Conroy | G01N 33/2882 702/25 |
| 2013/0182241 A1 * | 7/2013 | Lawandy | G01J 3/4406 356/51 |
| 2013/0188170 A1 * | 7/2013 | Wilkins | G01N 21/031 356/51 |
| 2013/0320237 A1 * | 12/2013 | Cadieux | G01N 21/64 250/459.1 |
| 2016/0101734 A1 * | 4/2016 | Baek | B60R 11/04 348/148 |
| 2016/0131629 A1 * | 5/2016 | Cadieux, Jr. | G01N 21/643 436/60 |
| 2016/0134609 A1 * | 5/2016 | Durham | H04L 63/08 726/7 |
| 2016/0239888 A1 * | 8/2016 | Silver | G06Q 30/0609 |
| 2016/0242448 A1 * | 8/2016 | Ludescher | A23G 9/42 |
| 2016/0275122 A1 * | 9/2016 | Kara | G06F 16/248 |
| 2016/0275699 A1 * | 9/2016 | Lu | H04N 9/0451 |
| 2017/0234819 A1 * | 8/2017 | Lilik | G01N 21/84 702/25 |
| 2017/0355081 A1 * | 12/2017 | Fisher | G05D 1/0016 |
| 2017/0364756 A1 * | 12/2017 | Liebau | G07C 5/08 |
| 2018/0149551 A1 * | 5/2018 | Okajima | G08B 21/18 |
| 2018/0293806 A1 * | 10/2018 | Zhang | G06T 7/0008 |

(56) References Cited

U.S. PATENT DOCUMENTS

| | | | | |
|---|---|---|---|---|
| 2018/0299355 A1* | 10/2018 | Young | ............... | G01N 15/06 |
| 2019/0024781 A1* | 1/2019 | Chrungoo | ............... | G08G 1/162 |
| 2019/0102622 A1* | 4/2019 | Spalenka | ............... | G06K 9/6215 |
| 2019/0170724 A1* | 6/2019 | Balagurusamy | ... | G01N 33/2858 |
| 2019/0383745 A1* | 12/2019 | Morton | ............... | G01N 21/65 |
| 2019/0384955 A1* | 12/2019 | Frieser | ............... | G07D 7/1205 |
| 2020/0200673 A1* | 6/2020 | Coates | ............... | G01N 21/31 |

FOREIGN PATENT DOCUMENTS

| | | |
|---|---|---|
| CN | 102680425 B | 8/2014 |
| CN | 106841083 A | 6/2017 |
| WO | WO2009080049 A1 | 7/2009 |
| WO | 2018056950 | 3/2018 |

OTHER PUBLICATIONS

English Translation of CN101726451A published Jun. 9, 2010, 5 pages.
English Translation of CN102680425B published Aug. 6, 2014, 12 pages.
English Translation of CN102830087A published Dec. 19, 2012, 7 pages.
English Translation of CN106841083A published Jun. 13, 2017, 12 pages.

* cited by examiner

SYSTEM AND METHOD FOR DETERMINING FLUID ORIGIN

TECHNICAL FIELD

The present disclosure relates to a system and method for determining the origin of a fluid, and more particularly, to determining the origin of a fluid based at least in part on spectral data associated with the fluid.

BACKGROUND

Fluids may be used in machines, for example, to provide an energy source, reduce friction between parts of the machine, cool parts of the machine, and/or operate hydraulic actuators. For example, a lubricant may be used to reduce friction between parts and/or to prevent the accumulation of heat during operation of the machine. There are a wide variety of machines, and thus, a wide variety of fluids having different characteristics selected for particular machines. If a fluid not having the proper characteristics is used in a machine, it may lead to premature wear or damage to the machine. For example, an operator or service technician of the machine may erroneously add fluid, or replace fluid in the machine, with fluid having improper characteristics for the machine, which may lead to premature wear or damage to the machine. If the machine is under warrantee or subject to a service contract, the manufacturer of the machine or a third party responsible for honoring the warrantee or service contract may suffer unnecessary expenses associated with repairing or replacing the machine as a result of the use of an improper fluid. However, it is often difficult to determine whether an improper fluid has been added to the machine or to identify the improper fluid with a high degree of certainty.

An attempt to monitor oil condition or quality is described in International Publication No. WO 2009/080049 A1 ("the '049 publication") to Olsen et al., published Jul. 2, 2009. Specifically, the '049 publication describes a method and a device for monitoring oil condition and/or quality based on fluorescence and/or near infrared (NIR) spectra, as well as laboratory reference measurements on a set of oil samples. According to the '049 publication, through the use of chemometric data analysis (i.e., multivariate data analysis), the spectroscopic signals and patterns are correlated to the laboratory reference measurements that describe the condition and/or quality of the oil. Based on this relation, according to the '049 publication, it is possible to predict the reference measurements and/or conditions of a new oil sample based solely on a fluorescence and/or NIR spectrum of the sample.

Although the method and device of the '049 publication are purported to monitor oil condition and/or quality, they do not purport to be able to determine the origin of a fluid or identify the fluid. Thus, the method and device of the '049 publication may not be useful to determine whether an improper fluid has been added to a machine or used to replace a fluid in the machine. In addition, the method and device of the '049 publication may not be able to identify or determine the origin of fluid in the machine.

The system and method disclosed herein may be directed to mitigating or overcoming one or more of the possible drawbacks set forth above.

SUMMARY

According to a first aspect, a system for determining an origin of a fluid from a machine may include a spectral measurement device configured to generate spectral data for a fluid. The system may also include a transmitter in communication with the spectral measurement device and configured to transmit the spectral data, and a receiver in communication with the transmitter and configured to receive a transmission indicative of the spectral data from the transmitter. The system may also include one or more processors in communication with the receiver and configured to cause execution of an analytical model configured to determine, based at least in part on the spectral data, fluidic information related to the fluid, the fluidic information including an indication of an origin of the fluid. The system may further include an output device in communication with the processor and configured to output the indication of the origin of the fluid.

According to a further aspect, a method for determining an origin of a fluid from a machine may include generating spectral data for the fluid and communicating the spectral data to one or more processors. The method may also include executing, via the one or more processors, a fluidic information model developed by a machine learning engine, the fluidic information model configured to determine, based at least in part on the spectral data, fluidic information related to the fluid. The fluidic information may include an indication of an origin of the fluid. The method may also include outputting an indication of the origin of the fluid.

According to another aspect, a computer-readable storage medium having computer-executable instructions stored thereupon which, when executed by a computer, may cause the computer to receive spectral data for a lubricant from a machine. The computer-executable instructions may also cause the computer to execute a fluidic information model developed by a machine learning engine, the fluidic information model configured to determine, based at least in part on the spectral data, fluidic information related to the lubricant. The fluidic information may include an indication of an origin of the lubricant. The computer-executable instructions may also cause the computer to output an indication of the origin of the lubricant to an output device.

BRIEF DESCRIPTION OF THE DRAWINGS

The detailed description is described with reference to the accompanying figures. In the figures, the left-most digit of a reference number identifies the figure in which the reference number first appears. The same reference numbers in different figures indicate similar or identical items.

DETAILED DESCRIPTION

Figure 1:
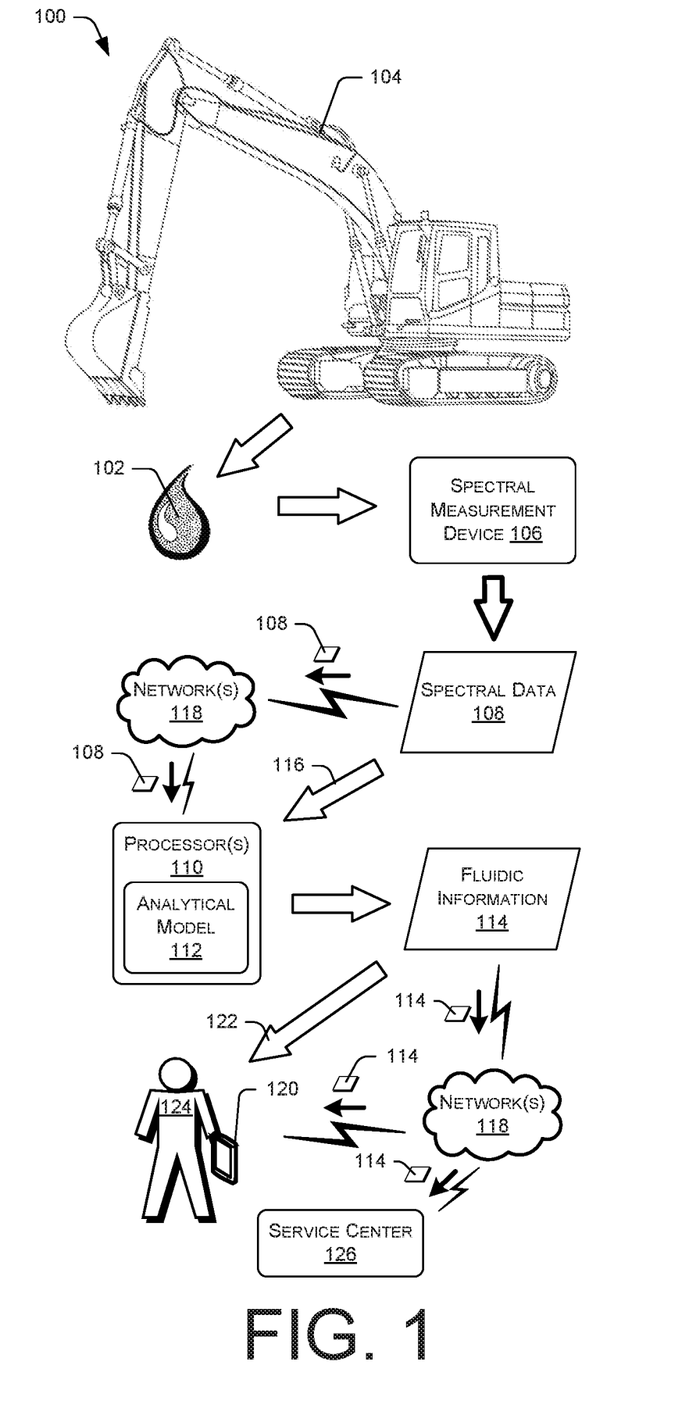
FIG. 1 illustrates a pictorial flow diagram of an example process for determining fluidic information of an example fluid from an example machine and displaying the fluidic information.

FIG. 1 illustrates a pictorial flow diagram of an example process 100 for determining fluidic information of an example fluid 102 from an example machine 104 and displaying the fluidic information. The fluid 102 may include, for example, one or more of fuel, lubricants, coolants, and/or hydraulic fluid used by machines. Other types of fluids are contemplated. The example machine 104 shown in FIG. 1 is an excavator. However, the machine 104 may be any type of machine configured to operate with moving parts, such as, for example, a generator, an internal combustion engine, a transmission, an automobile, a truck, an agricultural vehicle, and/or a construction vehicle, such as, for example, a dozer, a skid-steer loader, a grader, an on-highway truck, an off-highway truck, and/or any other machine known to a person skilled in the art.

As shown in FIG. 1, the example process 100 may include communicating a portion of the fluid 102 to a spectral measurement device 106 configured to generate spectral data 108 associated with at least a portion of the fluid 102. In some example embodiments, the spectral measurement device 106 may be incorporated into the machine 104, for example, such that it is not necessary to remove the portion of the fluid 102 from the machine and transport the portion of the fluid 102 to the spectral measurement device 106 at a location remote from the machine 104. For example, the machine 104 may include a reservoir for containing at least a portion of the fluid 102 and/or fluid passages through which at least a portion of the fluid 102 may flow, and the spectral measurement device 106 may be in flow communication with the reservoir and/or one or more of the passages. In some such example embodiments, the flow communication between the machine 104 and the spectral measurement device 106 may be selectively controlled, for example, via a valve that may be operated manually and/or automatically, and/or which may be controlled on-site or remotely via one or more networks, for example, such as the network(s) described herein.

In some example embodiments, the spectral measurement device 106 may be located remotely from the machine 104, such that, for example, a portion of the fluid 102 is withdrawn from a portion of the machine 104 (e.g., from a reservoir and/or a fluid passage) and transported to a location at which the spectral measurement device 106 is present. Such a location may be in the vicinity of the machine 104 (e.g., at a job-site) or remote from the machine 104 and requiring shipment of the portion of the fluid 102 withdrawn from the machine 104 to a location at which the spectral measurement device 106 is present.

The spectral measurement device 106 may be any type of spectral measurement device known to those skilled in the art as being configured to receive a fluid sample and generate spectral data associated with the fluid. For example, the spectral measurement device 106 may include, for example, a spectrometer, a spectrophotometer, a spectroscope, and/or a spectrograph configured to measure properties of electromagnetic radiation associated with a substance (e.g., a fluid), for example, over at least a portion of the electromagnetic spectrum. In some example embodiments, the spectral measurement device may be configured to generate one or more of a transmittance spectrum (e.g., an infrared spectrum) or an emission spectrum associated with the fluid. For example, the spectral measurement device 106 may include an infrared spectrometer configured to generate an infrared spectrum associated with the fluid 102. For example, the spectral measurement device 106 may be configured to generate a near-infrared spectrum associated with the fluid (e.g., from 4,000 to 14,000 $cm^{-1}$), a mid-infrared spectrum associated with the fluid (e.g., from 400 to 4,000 $cm^{-1}$), and/or a far-infrared spectrum associated with the fluid (e.g., from 10 to 400 $cm^{-1}$).

In some example embodiments, the spectral measurement device 106 may be configured to be used in a hand-held manner. For example, the spectral measurement device 106 may be compact and sufficiently light-weight for a person or machine to carry the spectral measurement device on-site in the vicinity of the machine 104. In some such example embodiments, a person or machine carrying the spectral measurement device 106 may communicate a portion of the fluid 102 directly from the machine 104 into the spectral measurement device 106, for example, as described herein. Once the portion of the fluid 102 has been communicated to the spectral measurement device 106, in some example embodiments, the spectral measurement device 106 may generate the spectral data 108 on-site or remotely from the machine 104. In some example embodiments, the spectral measurement device 106 may not be portable, for example, such as a spectral measurement device 106 in a laboratory setting or in a service center setting.

As shown in FIG. 1, the spectral data 108 may be communicated to one or more processor(s) 110 configured to cause execution of an analytical model 112 configured to determine, based at least in part on the spectral data 108 (e.g., a transmittance spectrum (e.g., an infrared spectrum) and/or an emission spectrum), fluidic information 114 related to the fluid 102. In some example embodiments, the analytical model 112 may be developed by a machine learning engine, for example, as described herein with respect to FIG. 2.

In some example embodiments, the fluidic information 114 may include an indication of an origin of the fluid 102. For example, the indication of the origin of the fluid 102 may include information related to one or more of an entity that manufactured the fluid 102, a brand associated with the fluid 102, a tradename and/or trademark under which the fluid 102 is marketed, and/or a geographic source of the fluid 102. In some example embodiments, the analytical model 112, based at least in part on the spectral data 108 (e.g., a transmittance spectrum (e.g., an infrared spectrum) and/or an emission spectrum), may be configured to determine the fluidic information 114, which may include information related to an item designation of the fluid 102, and the item designation may include one or more of a designation indicative of a type of the fluid (e.g., a lubricant, coolant, hydraulic fluid, fuel, etc.), a designation indicative of a viscosity of the fluid (e.g., for a lubricant), a designation indicative of additives in the fluid (e.g., for a lubricant or fuel), or a designation of a grade of the fluid (e.g., for a lubricant). In some example embodiments, the item designation may include a part number and/or item number associated with the fluid 102, for example, a unique textual identifier, a unique numeric identifier, or a unique alphanumeric identifier associated with the fluid 102. In some example embodiments, the spectral data 108 may include an emission spectrum associated with the fluid 102, and the fluidic information 114 may include, for example, an indication of detection of a contaminate in the fluid 102 or detection of metal in the fluid 102. For example, the analytical model 112 may be configured to detect, based at least in part on the spectral data 108 (e.g., an emission spectrum), a contaminate in the fluid and/or detect metal in the fluid.

The processor(s) 110 may operate to perform a variety of functions, as set forth herein. In some examples, the processor(s) 110 may include a central processing unit (CPU), a graphics processing unit (GPU), both CPU and GPU, or other processing units or components known in the art. Additionally, at least some of the processor(s) 110 may possess local memory, which also may store program modules, program data, and/or one or more operating systems. The processor(s) 110 may interact with, or include, computer-readable media, which may include volatile memory (e.g., RAM), non-volatile memory (e.g., ROM, flash memory, miniature hard drive, memory card, or the like), or some combination thereof. The computer-readable media may be non-transitory computer-readable media. The computer-readable media may be configured to store computer-executable instructions, which when executed by a computer, perform various operations associated with the processor(s) 110 to perform the operations described herein. The output device 120 may also include additional components not listed above that may perform any function associated with the output device 120.

Example embodiments may be provided as a computer program item including a non-transitory machine-readable storage medium having stored thereon instructions (in compressed or uncompressed form) that may be used to program a computer (or other electronic device) to perform processes or methods described herein. The machine-readable storage medium may include, but is not limited to, hard drives, floppy diskettes, optical disks, CD-ROMs, DVDs, read-only memories (ROMs), random access memories (RAMs), EPROMs, EEPROMs, flash memory, magnetic or optical cards, solid-state memory devices, or other types of media/ machine-readable medium suitable for storing electronic instructions. Further, example embodiments may also be provided as a computer program item including a transitory machine-readable signal (in compressed or uncompressed form). Examples of machine-readable signals, whether modulated using a carrier or not, include, but are not limited to, signals that a computer system or machine hosting or running a computer program can be configured to access, including signals downloaded through the Internet or other networks.

As shown in FIG. 1, the spectral data 108 may be communicated to the one or more processor(s) 110, either directly (e.g., as schematically depicted by the arrow 116) or via one or more network(s) 118. For example, the spectral data 108 may be communicated directly via a hard-wired connection to the one or more processor(s) 110, which may be an integral part of the spectral measurement device 106, may be located in the same general vicinity as the spectral measurement device 106 (e.g., in the same room or the same building), or may be located remotely from the spectral measurement device 106, but in communication via a hard-wired connection. In at least some example embodiments in which the spectral data 108 may be communicated to the one or more processor(s) 110 via one or more network(s) 118, the one or more network(s) 118 may include any type of network, such as a public wide-area-network (WAN) (e.g., the Internet), which may utilize various different technologies including wired and wireless technologies.

Once generated by the analytical model 112, the fluidic information 114 may be communicated to an output device configured to output the indication of the origin of the fluid 102 and/or other fluidic information. For example, as shown in FIG. 1, the fluidic information 114 may be communicated to an output device 120 configured to display the indication of the origin of the fluid 102 and/or other fluidic information, either directly (e.g., as schematically depicted by the arrow 122) or via the one or more network(s) 118, which may be the same or different than the one or more networks(s) 118 that may be used to communicate the spectral data 108 to the one or more processor(s) 110. For example, the fluidic information 114 may be communicated directly via a hard-wired connection to the output device 120, which may be an integral part of a device associated with the one or more processor(s) 110, may be located in the same general vicinity as the one or more processor(s) 110 (e.g., in the same room or the same building), or may be located remotely from the one or more processor(s) 110, but in communication via a hard-wired connection.

As shown in FIG. 1, in some example embodiments, the output device 120 may be a hand-held device configured to be portable by a person 124. For example, the output device 120 may include any computer device including a transceiver for sending and receiving signals, for example, via the one or more network(s) 118. For example, the output device 120 may be configured to display a user interface configured to display a representation of the fluidic information 114. In some examples, the fluidic information 114 may be communicated, either directly or via the one or more network(s) 118, to an output device 120 at a service center 126, which may be, for example, a location at which the condition, operation, and/or maintenance of the machine 104 may be monitored, or at which service and/or maintenance of the machine 104 may be performed, such as, for example, a location associated with the manufacturer of the machine and/or a location associated with a third party responsible for fulfilling a service and/or maintenance contract associated with the machine.

Figure 2:
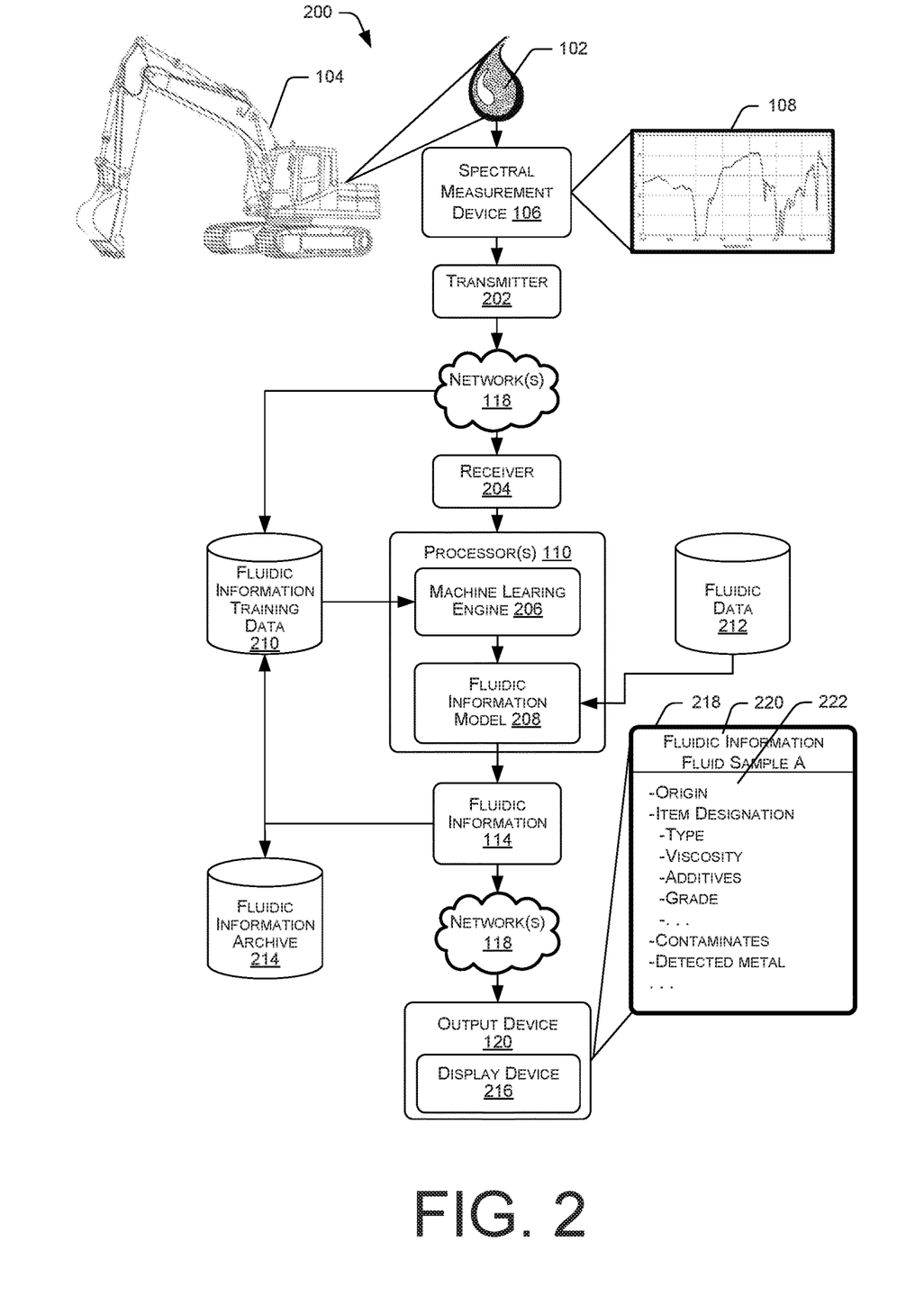
FIG. 2 illustrates an example system including an example flow of information for determining fluidic information of an example fluid from an example machine and displaying the fluidic information via an example display.

FIG. 2 illustrates an example system 200 including an example flow of information for determining fluidic information 114 of an example fluid 102 from an example machine 104 and displaying the fluidic information 114 via an example output device 120. As shown in FIG. 2, a portion of fluid 102 from the machine 104 may be communicated to a spectral measurement device 106 configured to generate spectral data 108 associated with at least a portion of the fluid 102, for example, as described herein.

As shown in FIG. 2, in some example embodiments, the spectral data 108 may be communicated via a transmitter 202 to the one or more processor(s) 110, either directly or via the one or more network(s) 118. The system 200 may also include a receiver 204 in communication with the one or more processor(s) 110 and configured to receive the spectral data 108 from the transmitter 202 via the one or more network(s) 118, for example, as described herein. In some example embodiments, the one or more processor(s) 110 may include a machine learning engine 206 configured to develop a fluidic information model 208 configured to determine, based at least in part on the spectral data 108 (e.g., a transmittance spectrum (e.g., an infrared spectrum) and/or an emission spectrum), the fluidic information 114 related to the fluid 102, for example, an indication of an origin of the fluid 102. Although FIG. 2 schematically depicts the machine learning engine 206 and the fluidic information model 208 as part of the same processor(s) 110 block, the machine learning engine 206 may be in one or more processors that are different from the one or more processors in which the fluidic information model 208 is executed.

For example, the system 200 may communicate the spectral data 108 to the fluidic information model 208, and the fluidic information model 208 may, in some example embodiments, generate the fluidic information 114, based at least in part on the spectral data 108. In some such example embodiments, the machine learning engine 206 may be used to train the fluidic information model 208, which may be configured to generate the fluidic information 114. In some examples, the machine learning engine 206 may be used to train the fluidic information model 208 via fluid information training data 210 used as ground truth data, for example, correlating characteristics of the spectral data 108 with fluidic information 114, including an indication of the origin of the fluid. In some example embodiments, the fluid information training data 210 may include data associated with a plurality of previous interactions, and/or other feedback or interaction with the fluidic information model 208, such as, for example, the fluidic information 114 generated by the fluidic information model 208.

In some example embodiments, confidence levels may be associated with the fluidic information 114, and the confidence levels may provide an indication of the relative confidence of the accuracy of the fluidic information. In some example embodiments, the confidence levels may be communicated to the output device 120 for display with (or independent of) the fluidic information 114. In some example embodiments, confidence levels may be provided for each of one or more of the types of information included in the fluidic information 114, such as, for example, information related to an origin of the fluid 102, an item designation of the fluid 102, an indication of the of a type of the fluid (e.g., a lubricant, coolant, hydraulic fluid, fuel, etc.), a designation indicative of a viscosity of the fluid (e.g., for a lubricant), a designation indicative of additives in the fluid (e.g., for a lubricant), and/or a designation of a grade of the fluid (e.g., for a lubricant). The machine learning engine 206 may employ one or more algorithms, such as supervised learning algorithms (e.g., artificial neural networks, Bayesian statistics, support vector machines, decision trees, random forest, classifiers, k-nearest neighbor, etc.), unsupervised learning algorithms (e.g., artificial neural networks, association rule learning, hierarchical clustering, cluster analysis, etc.), semi-supervised learning algorithms, deep learning algorithms, etc.

As shown in FIG. 2, in some example embodiments, the fluidic information model 208 may be configured to receive fluidic data 212 related to the fluid 102, and determine, based at least in part on the spectral data 108 and the fluidic data 212, the fluidic information 114 (e.g., an indication of the origin of the fluid 102). For example, the fluidic data 212 may include data related to one or more of time of operation of the machine 104 (e.g., during which the fluid 102 is in the machine 104), viscosity of the fluid 102, density of the fluid 102, temperature of the fluid 102 (e.g. during operation of the machine 104), a dielectric constant of the fluid 102, oxidation of the fluid 102, nitration of the fluid 102, sulfation of the fluid 102, or soot in the fluid 102. Other types of fluidic data 212 are contemplated. In some example embodiments, the fluidic data 212 may be determined based at least in part on the spectral data 108 and/or provided by other sources of information relating to the fluidic data 212.

As shown in FIG. 2, in some example embodiments, the fluidic information 114, along with the corresponding spectral data 108, may be communicated and added to the fluidic information training data 210, for example, so that the fluidic information 114 and corresponding spectral data 108 may be used to further train the fluidic information model 208, which may improve the accuracy of the fluidic information model 208 with use or over time. In some example embodiments, if the confidence level associated with the accuracy of the fluidic information 114 is below a threshold, such fluidic information 114 may not be communicated to the fluidic information training data 210 or the effect of such fluidic information 114 on training the machine learning engine 206 may be discounted, for example, based at least in part on the confidence level.

As shown in FIG. 2, the fluidic information 114 may be communicated to an output device 120 configured to output the indication of the origin of the fluid 102 and/or other fluidic information. In some example embodiments, the fluidic information may be communicated via a transmitter in communication with the one or more processor(s) 110 and the output device 120. For example, in some example embodiments, the receiver 204 may be a transceiver, and the transceiver may be configured to communicate the fluidic information 114 to the output device 120. In some example embodiments, the fluidic information 114 may be communicated to a fluidic information archive 214 for storage as, for example, predicted fluidic information for possible later use. The fluidic information archive 214 may be stored in memory together with, or separate from, other memory associated with the system 200.

As shown in FIG. 2, in some example embodiments, the output device 120 may include a display device 216 configured to display the indication of the origin of the fluid 102 and/or other fluidic information. For example, the display device 216 may include a display associated with a computer configured to display a user interface 218, for example, as shown in FIG. 2. For example, the user interface 218 may include a banner 220 configured to display an identifier associated with the fluid 102 corresponding to the spectral data 108 generated by the spectral measurement device 106 (e.g., "Fluidic Information Fluid Sample A"), and a fluidic information field 222 configured to display the fluidic information 114 associated with the fluid 102, such as, for example, the fluidic information 114 described herein. The display of other types of fluidic information and associated information is contemplated.

Figure 3:
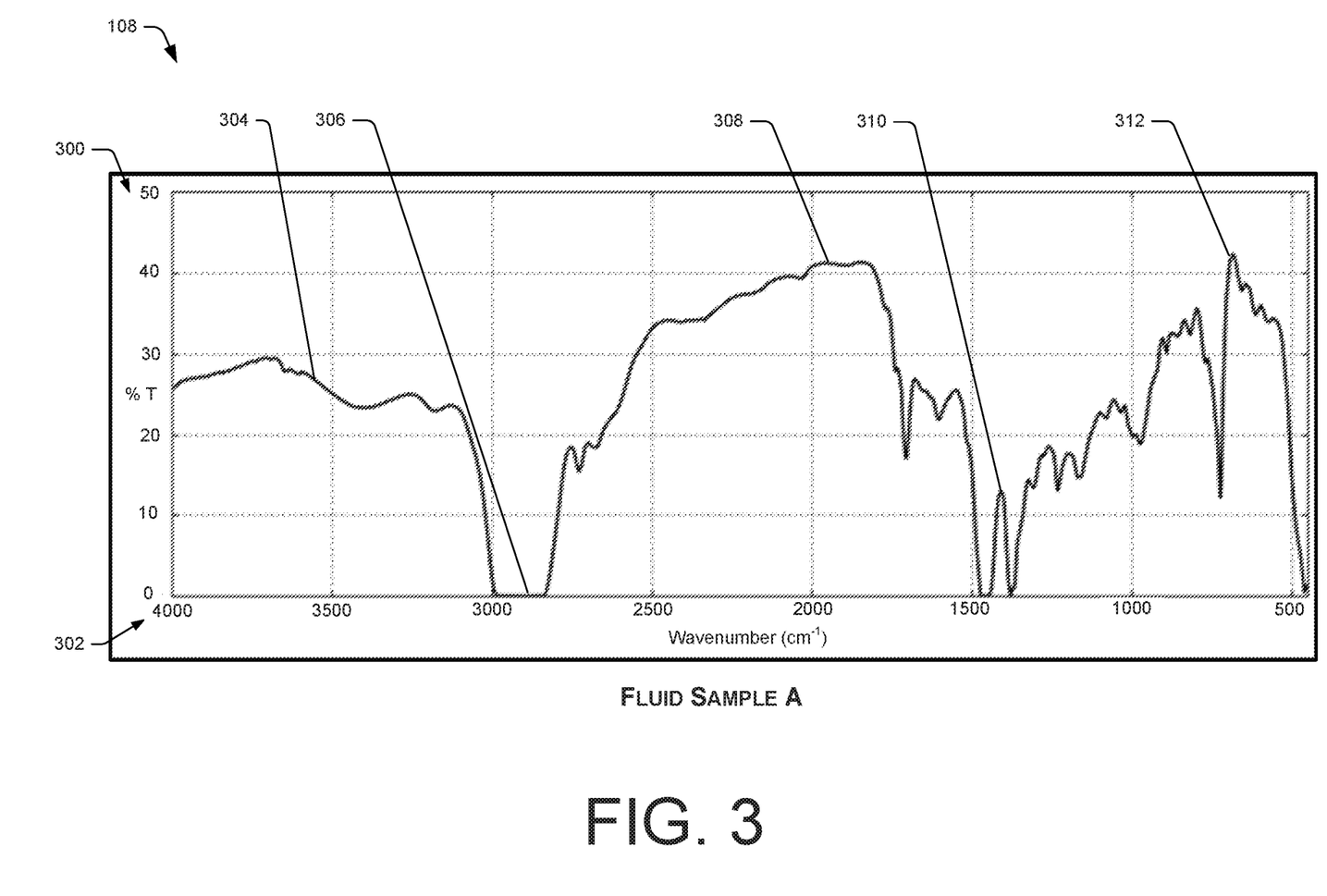
FIG. 3 is an example transmittance spectrum of an example fluid.

FIG. 3 is an example of spectral data 108 including a transmittance spectrum of an example fluid 102. In the example shown in FIG. 3, the spectral data 108 includes the percent transmittance 300 (% T) on a vertical axis and a wavenumber 302 (cm$^{-1}$) on a horizontal axis. The example spectral data 108 shown in FIG. 3 ranges from 4000 cm$^{-1}$ to 500 cm$^{-1}$. Other ranges are contemplated. In the example shown, the spectral data 108 includes an example plot 304 of the percent transmittance 300 of the example fluid 102 ("Fluid Sample A") versus the wavenumber 302. The example plot 304 includes several points 306, 308, 310, and 312 that may be unique to, characteristic of, and/or indicative of the fluidic information 114 associated with the example fluid 102. For example, the point 306 indicates the example fluid 102 has zero transmittance ranging from about 3000 cm$^{-1}$ to about 2800 cm$^{-1}$, and at point 308, a relatively constant and high transmittance of about 40% ranging from about 2100 cm$^{-1}$ to about 175 cm$^{-1}$, before dropping steeply beginning at about 1750 cm$^{-1}$ to zero transmittance slightly below about 1500 cm$^{-1}$. At point 310, the example fluid 102 has a transmittance spike at about 1450 cm$^{-1}$ to about 13% transmittance, and at point 312 a peak transmittance of about 42% at about 700 cm$^{-1}$. One or more of the points 306, 308, 310, or 312, and/or other characteristics of the example plot 304, may be unique to the example fluid 102, and the analytical model 112 (e.g., the fluidic information model 208) may be configured to generate the fluidic information 114 based at least in part on one or more unique aspects of the plot 304, either alone or in addition to other information, such as, for example, the fluidic data 212, as described herein.

Figure 4:
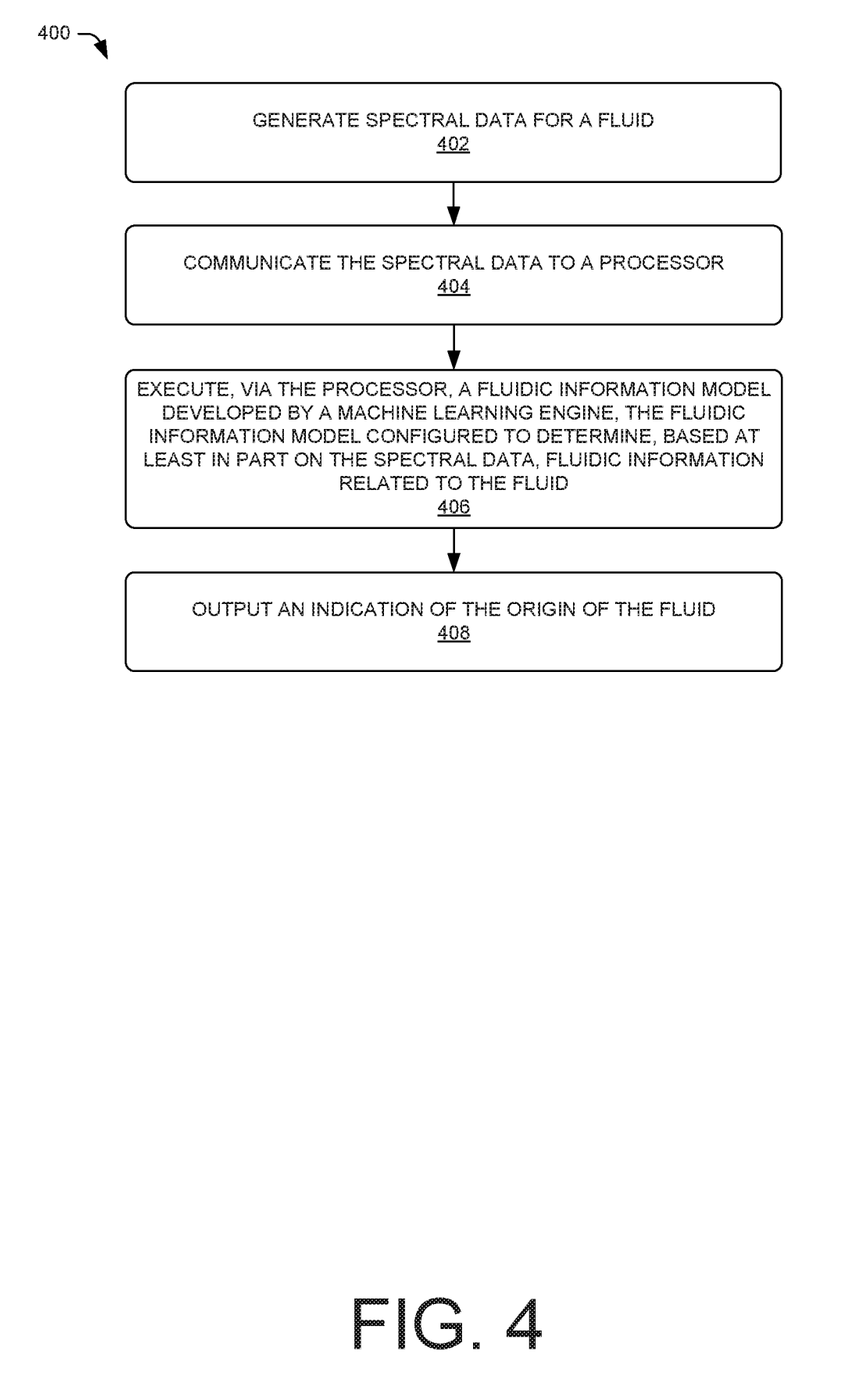
FIG. 4 is a block diagram of an example process for outputting an indication of the origin of a fluid.

FIG. 4 illustrates an example process for outputting an indication of the origin of a fluid. This process is illustrated as a logical flow graph, operation of which represents a sequence of operations, at least some of which may be implemented in hardware, software, or a combination thereof. In the context of software, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described operations can be combined in any order and/or in parallel to implement the process.

FIG. 4 illustrates a flow diagram of an example process 400 for outputting an indication of the origin of a fluid based at least in part on spectral data (e.g., a transmittance spectrum (e.g., an infrared spectrum) and/or an emission spectrum) associated with the fluid, for example, as described herein. The following actions described with respect to FIG. 4 may be performed, for example, as illustrated with respect to FIGS. 1 and 2.

The example process 400, at 402, may include generating spectral data for the fluid. For example, generating spectral data for the fluid may include communicating the fluid to a spectral measurement device and generating via the spectral measurement device the spectral data for the fluid, for example, as described herein. In some example embodiments, communicating the fluid to the spectral measurement device may include removing a sample of the fluid from the machine and introducing the sample of the fluid to the spectral measurement device, for example, as described herein. In some example embodiments, communicating the fluid to the spectral measurement device may include operating a valve configured to facilitate the flow of fluid from one or more of a fluid reservoir of the machine or one or more fluid passages of the machine to provide flow communication to the spectral measurement device, for example, as described herein. In some example embodiments, generating the spectral data for the fluid may include generating one or more of a transmittance spectrum (e.g., an infrared spectrum, for example, generated via an infrared spectrometer) or an emission spectrum for the fluid, as described herein.

At 404, the process 400, in some examples, may include communicating the spectral data to one or more processors. For example, communicating the spectral data to the one or more processors may include wirelessly communicating the spectral data to a location remote from the spectral measurement device, for example, as described herein.

At 406, the example process 400 may include executing, via the one or more processors, a fluidic information model developed by a machine learning engine, the fluidic information model being configured to determine, based at least in part on the spectral data, fluidic information related to the fluid. In some example embodiments, the fluidic information may include an indication of an origin of the fluid. In some example embodiments, executing the fluidic information model may include executing the fluidic information model to determine an item designation of the fluid based at least in part on the spectral data (e.g., a transmittance spectrum and/or an emission spectrum), and the item designation may include, for example, at least one of a designation indicative of a type of the fluid, a designation indicative of a viscosity of the fluid, a designation indicative of additives in the fluid, or a designation of a grade of the fluid. In some example embodiments, the spectral data may include an emission spectrum, and executing the fluidic information model includes executing the fluidic information model to at least one of detect a contaminate in the fluid or detect metal in the fluid. In some example embodiments, the example process 400 may include communicating to the one or more processors fluidic data associated with the fluid, and executing the fluidic information model to determine, based at least in part on the spectral data and the fluidic data, the origin of the fluid. The fluidic data may include, for example, information related to at least one of time of operation of the machine, viscosity of the fluid, density of the fluid, temperature of the fluid, a dielectric constant of the fluid, oxidation of the fluid, nitration of the fluid, sulfation of the fluid, or soot in the fluid.

The example process 400 may also include, at 408, outputting an indication of the origin of the fluid and/or other fluidic information. In some example embodiments, outputting an indication of the origin of the fluid and/or the fluidic information may include communicating the fluidic information, either directly or via one or more networks, to an output device at a service center, which may be, for example, a location at which the condition, operation, and/or maintenance of the machine may be monitored, or at which service and/or maintenance of the machine may be performed. In some example embodiments, the output device may be a hand-held device configured to be portable by a person. For example, the display device may be any type of device configured to convey fluidic information to a person, such as, for example, a device configured to display a user interface displaying a representation of the fluidic information.

INDUSTRIAL APPLICABILITY

The exemplary system and method of the present disclosure may be applicable to a variety of fluid types and may be used to determine, based at least in part, on spectral data of the fluid, fluidic information associated with the fluid, such as, for example, the origin of the fluid. For example, the fluid types may include, for example, lubricants, coolants, hydraulic fluid, fuel, etc. The origin of the fluid may include, for example, a brand associated with the fluid, a tradename and/or trademark under which the fluid is marketed, and/or a geographic source of the fluid. In some example embodiments, the system and method may be used to determine, based at least in part on the spectral data, other fluidic information, for example, as described herein, such as, for example, an item designation of the fluid. The item designation of the fluid may include one or more of a designation indicative of a type of the fluid (e.g., a lubricant, coolant, hydraulic fluid, fuel, etc.), a designation indicative of a viscosity of the fluid, a designation indicative of additives in the fluid, or a designation of a grade of the fluid. In some example embodiments, the item designation may include a part number and/or item number associated with the fluid, for example, a unique textual identifier, a unique numeric identifier, or a unique alphanumeric identifier associated with the fluid. In some example embodiments of the system and method, the fluidic information may be determined based at least in part on the spectral data and fluidic data related to the fluid. The fluidic data may include data related to one or more of time of operation of the machine (e.g., during which the fluid is in the machine), viscosity of the fluid, density of the fluid, temperature of the fluid (e.g., during operation of the machine), a dielectric constant of the fluid, oxidation of the fluid, nitration of the fluid, sulfation of the fluid, soot in the fluid, or other types of fluidic data. The fluidic data may be determined based at least in part on the spectral data of the fluid and/or provided by other sources of information relating to the fluidic data.

Determining fluidic information associated with a fluid may be useful in many situations. As noted above, fluids may be used in machines, for example, to provide an energy source, reduce friction between parts, provide a coolant, and/or to operate hydraulic actuators. There are a wide variety of machines, and thus, a wide variety of fluids having different characteristics selected for particular machines. If a fluid not having the proper characteristics is used in a machine, it may lead to premature wear or damage to the machine. If a machine exhibits premature wear or damage, it may be due at least in part to the use of fluid not having the proper characteristics for the intended use. However, it may be difficult to determine whether an improper fluid was added to the machine or used as a replacement for a proper fluid. Some example embodiments of the system and method disclosed herein may render it possible to determine whether a fluid having improper characteristics was added to or used as a replacement in the machine.

For example, the origin of the fluid may be an indication of the brand, manufacturer, and/or source of the fluid, which may provide an indication of whether a fluid having the correct characteristics was used in the machine. The item designation, in some examples, may provide an indication of whether a fluid having the correct characteristics was used in the machine, even if the origin of the fluid is consistent with an origin from which a fluid having the correct characteristics may be obtained. Other fluidic information, such as the other fluidic information described herein, may provide other valuable information about the fluid and/or operation of the machine from which a sample of the fluid was taken, such as, for example, whether the fluid is past its service life and/or whether certain types of damage have occurred to parts of the machine. For example, certain chemical characteristics associated with the fluid sample (e.g., unexpectedly high oxidation or soot levels) may be an indication of the fluid needing to be replaced. Unexpectedly high levels of metal in the fluid sample may indicate excessive wear or damage to the machine.

In some example embodiments of the system and method, the fluidic information may be obtained and reported locally. For example, a sample of the fluid may be manually withdrawn from the machine and transferred to a spectral measurement device located in the vicinity of the machine, such as at a job-site where the machine is being operated. The spectral measurement device may generate the spectral data of the fluid, which may be communicated to one or more processors configured to execute the analytical model configured to determine the fluidic information based at least in part on the spectral data. In some example embodiments, the spectral measurement device may be incorporated into the machine, for example, as discussed herein, and the spectral data may be generated without removing fluid from the machine. In some example embodiments, the one or more processors may be located in the vicinity of the machine and/or the spectral measurement device. In such instances, on-site service or maintenance personnel may determine the fluidic information. In some example embodiments, the one or more processors may be located remotely from the machine, for example, at an off-site service center, and the spectral data may be communicated to the one or more processors via one or more networks, for example, as described herein. In such examples, service or maintenance personnel located remotely from the job-site may be provided with the fluidic information.

While aspects of the present disclosure have been particularly shown and described with reference to the embodiments above, it will be understood by those skilled in the art that various additional embodiments may be contemplated by the modification of the disclosed machines, systems, and methods without departing from the spirit and scope of what is disclosed. Such embodiments should be understood to fall within the scope of the present disclosure as determined based upon the claims and any equivalents thereof.

What is claimed is:

1. A system for determining an origin of a fluid from a machine, the system comprising:
   a spectral measurement device configured to generate spectral data for the fluid;
   a transmitter in communication with the spectral measurement device and configured to transmit the spectral data;
   a receiver in communication with the transmitter and configured to receive a transmission indicative of the spectral data from the transmitter;
   a processor in communication with the receiver and configured to cause execution of a fluidic information model developed by a machine learning engine, wherein:
      the fluidic information model is trained by the machine learning engine to generate, based at least in part on the spectral data, fluidic information related to the fluid, and
      the fluidic information includes at least an indication of the origin of the fluid that identifies at least one of:
         a manufacturer of the fluid,
         a brand associated with the fluid, or
         a geographic source of the fluid; and
   an output device in communication with the processor and configured to output the indication of the origin of the fluid and a confidence level for the indication of the origin of the fluid.

2. The system of claim 1, wherein the spectral measurement device comprises an infrared spectrometer configured to generate a transmittance spectrum for the fluid.

3. The system of claim 1, wherein the machine learning engine is configured to re-train the fluidic information model based at least in part on the fluidic information and the spectral data.

4. The system of claim 1, wherein the fluid includes a lubricant, and wherein the processor is further configured to execute the fluidic information model and determine an item designation of the lubricant based at least in part on the spectral data, the item designation indicating at least one of:
   a type of the lubricant,
   a viscosity of the lubricant,
   additives in the lubricant, or
   a grade of the lubricant.

5. The system of claim 1, wherein the spectral data includes an emission spectrum, and wherein the processor is further configured to execute the fluidic information model and, based at least in part on the emission spectrum, at least one of:
   detect a contaminate in the fluid, or
   detect metal in the fluid.

6. The system of claim 1, wherein the output device comprises a display device configured to display the indication of the origin of the fluid.

7. The system of claim 1, wherein the machine contains the fluid, and further comprising a coupling configured to:
   couple the spectral measurement device to the machine containing the fluid; and
   provide flow communication between the spectral measurement device and the fluid.

8. The system of claim 1,
   wherein the processor is further configured to receive fluidic data related to the fluid, wherein, when causing execution of the fluidic information model, the processor is configured to execute the fluidic information model to determine, based at least in part on the spectral data and the fluidic data, the origin of the fluid, and wherein the fluidic data includes data related to at least one of: a time of operation of the machine, a viscosity of the fluid, a density of the fluid, a temperature of the fluid, a dielectric constant of the fluid, an oxidation of the fluid, a nitration of the fluid, a sulfation of the fluid, or an indicator of soot in the fluid.

9. A method for determining an origin of a fluid from a machine, the method comprising:
generating spectral data for the fluid;
communicating the spectral data to a processor;
executing, via the processor, a fluidic information model developed by a machine learning engine, wherein:
the fluidic information model is trained by the machine learning engine to generate, based at least in part on the spectral data, fluidic information related to the fluid, and
the fluidic information includes at least an indication of the origin of the fluid that identifies at least one of:
a manufacturer of the fluid,
a brand associated with the fluid, or
a geographic source of the fluid; and
outputting the indication of the origin of the fluid and a confidence level for the indication of the origin of the fluid.

10. The method of claim 9, wherein generating the spectral data for the fluid includes communicating the fluid to a spectral measurement device and generating, via the spectral measurement device, the spectral data for the fluid.

11. The method of claim 10, wherein communicating the fluid to the spectral measurement device includes removing a sample of the fluid from the machine and introducing the sample of the fluid to the spectral measurement device.

12. The method of claim 9, wherein the processor is located at a location remote from a spectral measurement device that generates the spectral data, and communicating the spectral data to the processor includes wirelessly communicating the spectral data to the processor at the location remote from the spectral measurement device.

13. The method of claim 9, wherein generating the spectral data for the fluid includes generating an infrared spectrum for the fluid.

14. The method of claim 9, wherein executing the fluidic information model includes executing the fluidic information model to determine an item designation of the fluid based at least in part on the spectral data, the item designation indicating at least one of:
a type of the fluid,
a viscosity of the fluid,
additives in the fluid, or
a grade of the fluid.

15. The method of claim 9, wherein the spectral data includes an emission spectrum, and wherein executing the fluidic information model includes executing the fluidic information model to at least one of:
detect a contaminate in the fluid, or
detect metal in the fluid.

16. The method of claim 9, further comprising:
communicating, to the processor, fluidic data associated with the fluid,
wherein executing the fluidic information model comprises:
executing the fluidic information model to determine, based at least in part on the spectral data and the fluidic data, the origin of the fluid, and
wherein the fluidic data includes information related to at least one of: a time of operation of the machine, a viscosity of the fluid, a density of the fluid, a temperature of the fluid, a dielectric constant of the fluid, an oxidation of the fluid, a nitration of the fluid, a sulfation of the fluid, or an indicator of soot in the fluid.

17. A non-transitory computer-readable storage medium having computer-executable instructions stored thereupon which, when executed by a computer, cause the computer to:
receive spectral data for a lubricant associated with a machine;
execute a fluidic information model developed by a machine learning engine, wherein:
the fluidic information model is trained by the machine learning engine to generate, based at least in part on the spectral data, fluidic information related to the lubricant, and
the fluidic information includes at least an indication of an origin of the lubricant that identifies at least one of:
a manufacturer of the lubricant,
a brand associated with the lubricant, or
a geographic source of the lubricant; and
output the indication of the origin of the lubricant to an output device and a confidence level for the indication of the origin of the fluid.

18. The non-transitory computer-readable storage medium of claim 17, wherein the computer is further caused to execute the fluidic information model to determine, based at least in part on the spectral data, an item designation of the lubricant, the item designation indicating at least one of:
a type of the lubricant,
a viscosity of the lubricant, or
a grade of the lubricant.

19. The non-transitory computer-readable storage medium of claim 17, wherein the computer is further caused to execute the fluidic information model to, based at least in part on the spectral data, at least one of:
detect a contaminate in the lubricant, or
detect metal in the lubricant.

20. The non-transitory computer-readable storage medium of claim 17,
wherein the computer is further caused to:
receive fluidic data related to the lubricant,
wherein the fluidic information is generated further based on the fluidic data, and
wherein the fluidic data includes information related to at least one of: a time of operation of the machine, a viscosity of the lubricant, a density of the lubricant, a temperature of the lubricant, a dielectric constant of the lubricant, an oxidation of the lubricant, a nitration of the lubricant, a sulfation of the lubricant, or an indicator of soot in the lubricant.

* * * * *